United States Patent [19]

Ember et al.

[11] Patent Number: 5,334,771
[45] Date of Patent: Aug. 2, 1994

[54] PEROXIDATION OF SECONDARY CARBON IN ALKANES AND CYCLOALKANES

[75] Inventors: George Ember, Hackensack, N.J.; Edilberto A. De Castro Netro, Bahia; Rogerio F. De Lacerda, Ondina, both of Brazil

[73] Assignees: ABB Lummus Crest Inc., Bloomfield, N.J.; Nitrocarbono S.A., Camacari, Brazil

[21] Appl. No.: 91,780

[22] Filed: Jul. 14, 1993

[51] Int. Cl.$^5$ ............... C07C 409/04; C07C 409/06; C07C 409/08
[52] U.S. Cl. ................. 568/573; 568/570; 568/571; 568/576
[58] Field of Search ............... 568/568, 571, 573, 576, 568/570

[56] References Cited

U.S. PATENT DOCUMENTS

| | | | |
|---|---|---|---|
| 3,987,115 | 10/1976 | Zajacek et al. | 568/571 |
| 5,043,481 | 8/1991 | Nedwick | 568/570 |
| 5,196,597 | 3/1993 | Cochran et al. | 568/571 |
| 5,220,075 | 6/1993 | Ember | 568/573 |

*Primary Examiner*—Werren B. Lone
*Attorney, Agent, or Firm*—Chilton, Alix & Van Kirk

[57] ABSTRACT

A secondary carbon atom in an alkane, including alkyl groups attached to aromatic rings, or cycloalkane is peroxidized by molecular oxygen to the corresponding hydroperoxide in the absence of a catalyst. The peroxidation is carried out in the presence of a tertiary hydroperoxide initiator which provides the free radicals needed to maintain the reaction. The amount of tertiary alcohol in the initiator is limited. The initial product of the peroxidation contains the secondary hydroperoxide as well as unreacted hydrocarbon, unreacted tertiary hydroperoxide and tertiary alcohol. The tertiary alcohol is removed as an azeotrope with part of the unreacted hydrocarbon which may be then separated from the alcohol and recycled. A second azeotropic distillation follows where the unreacted tertiary hydroperoxide is removed as an azeotrope with the rest of the unreacted hydrocarbon. This azeotrope is directly recycled to the peroxidation reaction.

10 Claims, 1 Drawing Sheet

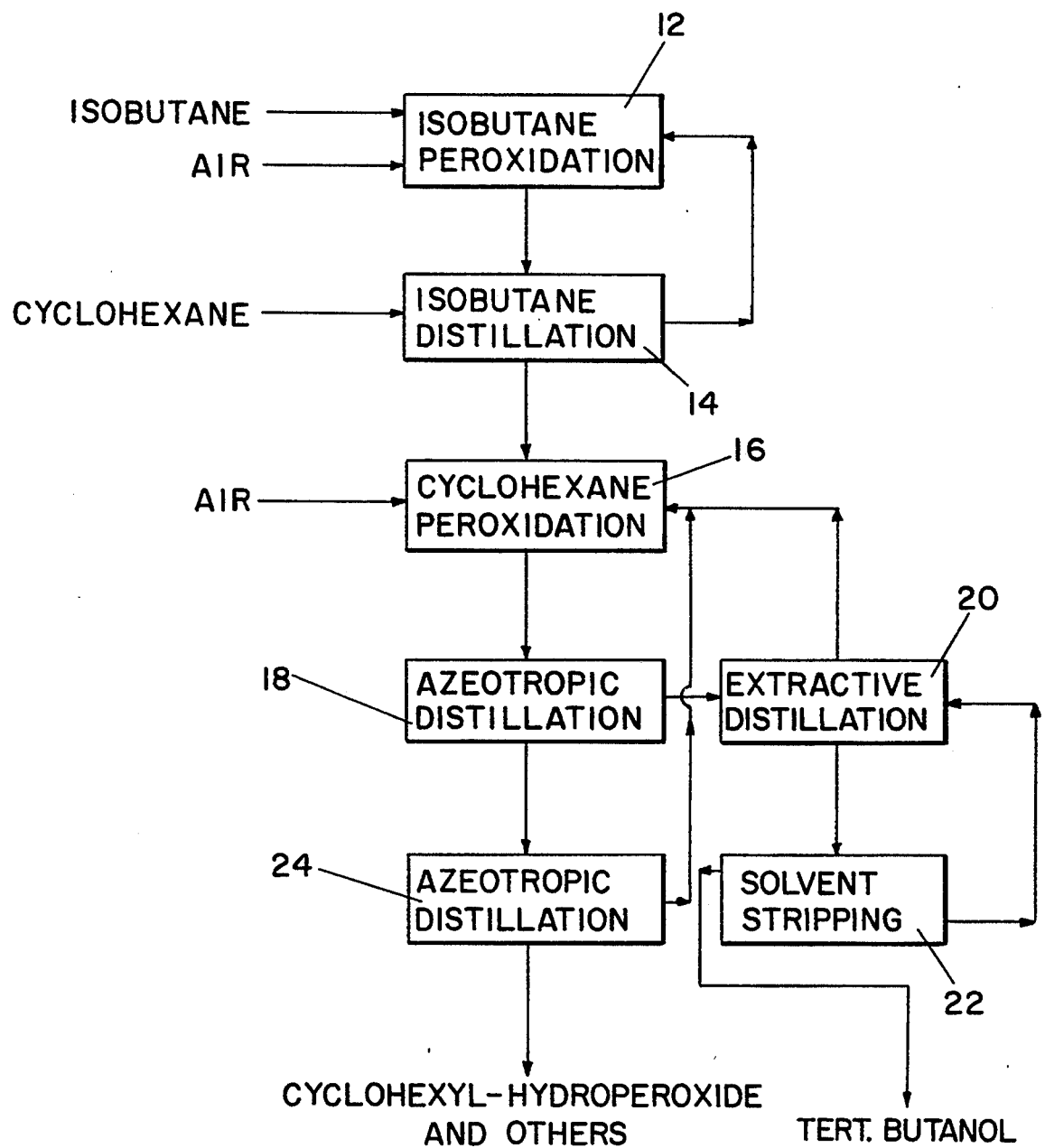

PEROXIDATION OF SECONDARY CARBON IN ALKANES AND CYCLOALKANES

BACKGROUND OF THE INVENTION

The present invention relates to the peroxidation of secondary carbon in alkanes, including alkyl groups attached to aromatic rings, and cycloalkanes using a hydroperoxide initiator.

It is well known that the various tertiary and secondary organic hydroperoxides are suitable as oxidants for a number of highly selective partial oxidations. Molecular oxygen is usually not very suitable for these oxidations since a selective or partial oxidation requires, in a stoichiometric sense, the transfer of one oxygen atom only. For example, organic hydroperoxides are particularly effective for the synthesis of alcohols, aldehydes, ketones, epoxides, cyanates and oximes.

Typical industrial processes for oxidizing alkanes and cycloalkanes involve oxidation in the presence of a catalyst such as a cobalt-naphthanate catalyst. The peroxide which is formed is only transitory and is subject to decomposition in the presence of the catalyst. The primary products are the corresponding alcohol and ketone. For example, the most widely used oxidation process for cyclohexane has only about 4 to 5% conversion of the cyclohexane and the product is about 75% cyclohexanol and cyclohexanone with the remainder being various by-products. At higher conversion levels, the selectivity of products decreases because the cyclohexanone is readily oxidized to by-products. The solution is to minimize the formation of the cyclohexanone by keeping the conversion of cyclohexane at a low level or preventing the formation of cyclohexanone from cyclohexanol such as by esterification. None of these processes produce any significant quantity of the peroxide, cyclohexyl hydroperoxide, in the final product. Typically the amount is only 5 to 10% of the product.

The main objective of peroxidations is the production of the corresponding hydroperoxides. However, the decomposition of hydroperoxides is required to maintain the free radical type chain reaction. This represents a loss in selectivity for the desired hydroperoxide. In addition, the alcohols or ketones formed from the decomposition of secondary hydroperoxides are more readily oxidized than the corresponding hydrocarbons. This over-oxidation leads to the rupture of carbon-carbon bonds and to the formation of carboxylic acids, which also facilitate the decomposition of the hydroperoxides. The result is a rapid decrease in the selectivity of products with increasing conversion.

To avoid this yield loss, the oxidation/peroxidation of the secondary carbon in various alkanes and cycloalkanes has to be carried out without the usual transition metal ions, which catalyze the decomposition of hydroperoxides. Also, the reactions have to be stopped at relatively low conversion levels. The commercial use of secondary carbon oxidations is limited by these two problems. First, in a non-catalytic oxidation, the initiation of the chain reaction must rely on the thermal decomposition of some hydroperoxide. This means that at low temperature the reaction is very slow while at high temperature the selectivity is low. Secondly, to produce the hydroperoxide of the secondary carbon at high selectivity, one can not rely on its decomposition for supplying the free radicals.

According to the invention described and claimed in U.S. Pat. No. 5,220,075 dated Jun. 15, 1993, a secondary carbon atom in an alkane, including alkyl groups attached to aromatic rings, or cycloalkane hydrocarbon is oxidized by molecular oxygen to the corresponding hydroperoxide in the absence of a catalyst. The oxidation is carried out in the presence of a tertiary hydroperoxide, which provides the free radicals needed to maintain the reaction. This method of reaction is particularly applicable to the peroxidation of cyclohexane to produce cyclohexyl hydroperoxide at a temperature of 100° to 200° C. and preferably 130° to 160° C. and a pressure of 700 to 1200 kPa using 0.5 to 10% and preferably 1 to 5% tertiary butyl hydroperoxide or tertiary amyl hydroperoxide. All percentages are expressed as mole percent unless otherwise noted. This method for the oxidation of the secondary carbon in alkanes and cycloalkanes results in a relatively high conversion and selectivity for the hydroperoxide.

Among the hydrocarbons which are commercially oxidized, cyclohexane and ethyl-benzene are industrially the most important and are used for the production of cyclohexyl hydroperoxide and ethylbenzylhydroperoxide. These are the key intermediates in the coproduction of propylene-oxide with styrene or with cyclohexanol. The propylene oxide, styrene and cyclohexanol are key components for the production of polymers such as polyurethane, polystyrene and nylon.

Due to the cost of the plant for producing the tertiary hydroperoxide initiators (i.e. tertiary butyl hydroperoxide and tertiary amyl hydroperoxide), the producers of ethylbenzene hydroperoxide and cyclohexane hydroperoxide would like to minimize the amount of initiator consumed per unit of secondary hydroperoxide that is produced. On the other hand, the effectiveness of the tertiary hydroperoxide for initiating the free radical type chain reaction and for achieving the optimum selectivity of the secondary hydroperoxide increases with the concentration of the tertiary hydroperoxide. An increase in the concentration of the initiator, tertiary hydroperoxide, results in a faster reaction and in an increased selectivity of products. This means lower capital and operating costs for the producer.

The effluent from the initiated peroxidation of a secondary hydrocarbon contains the secondary hydroperoxide product, the unreacted hydrocarbon and some alcohol. It will also contain considerable quantities of the tertiary hydroperoxide initiator, particularly, if the concentration of the initiator in the peroxidation reaction is maintained at a high level to improve the performance of the reaction.

SUMMARY OF THE INVENTION

An object of the present invention is to improve the effectiveness of an initiated peroxidation reaction by recovering and recycling some components of the reactor effluent. Due to the inherently low conversion obtainable in the oxidation of secondary hydrocarbons, a large amount of the unreacted hydrocarbon has to be recycled. While the minimum boiling azeotropes of these secondary hydrocarbons and the tertiary alcohols were known, it has been discovered that the secondary hydrocarbons also form binary azeotropes with the tertiary hydroperoxides. These azeotropes make the recovery of the tertiary alcohol and the recycle of the tertiary hydroperoxide possible. The intentional recycle of the tertiary hydroperoxide allows the efficient use of the initiator at concentrations above the economic optimum.

In particular, this invention is applicable to the peroxidation of secondary hydrocarbons such as cyclohexane and ethylbenzene with tertiary hydroperoxides, such as tertiary butyl hydroperoxide and tertiary amyl hydroperoxide. It has been found that the unreacted secondary hydrocarbon forms a binary azeotrope with the tertiary hydroperoxide. In practice, first the azeotrope of the tertiary alcohol and unreacted secondary hydrocarbon is recovered. This first azeotrope has a lower boiling point than the binary azeotrope of unreacted hydrocarbon and tertiary hydroperoxide. Pure tertiary butyl alcohol can be recovered from the first azeotrope by extractive distillation, using a strongly polar solvent (i.e. ethylene or propylene glycol) which boils above 100° C.

The second azeotrope of unreacted hydrocarbon and tertiary hydroperoxide is directly recycled back to the peroxidation reactor. By this recycle, a much higher concentration of tertiary hydroperoxide in the peroxidation reactor can be maintained than the economical optimum for a once through operation. The higher concentration of the initiator results in an increased rate of free radical formation which in turn leads to an increased reaction rate or it allows the peroxidation to be carried out at lower reaction temperature with increased selectivity of the secondary hydroperoxide. In addition, the consumption of tertiary butyl hydroperoxide and the formation of tertiary alcohol, a low priced by-product, are minimized. These operational advantages lead to the improvement of the overall economics of cyclohexane peroxidation.

BRIEF DESCRIPTION OF THE DRAWING

The drawing is a block flow diagram of the present invention showing a process scheme for the initiated peroxidation of cyclohexane involving the recycle of tertiary butyl hydroperoxide.

DESCRIPTION OF THE PREFERRED EMBODIMENTS

The present invention is applicable to the peroxidation of a variety of alkanes and cycloalkanes but will first be described with reference to peroxidation of cyclohexane to form cyclohexyl hydroperoxide.

The typical oxidation of cyclohexane relies on the catalytic decomposition of the cyclohexyl hydroperoxide to generate free radicals which are required to maintain the chain reaction. However, the decomposition of cyclohexyl hydroperoxide leads to the formation of cyclohexanol and cyclohexanone. The U.S. Pat. No. 5,220,075, minimizes the decomposition of cyclohexyl hydroperoxide by eliminating the catalyst and by decreasing the reaction temperature. Unless other steps were taken, this would result in a significant decrease in the reaction rate because of the drop in the concentration of free radicals available to carry out the reaction.

In order to regain a reaction rate comparable to the reaction rate of the catalytic process, the present invention adds a small amount (0.5 to 10% and preferably 1 to 5%) of a tertiary hydroperoxide such as tertiary butyl hydroperoxide or tertiary amyl hydroperoxide to the cyclohexane fed to the oxidation reactor. These tertiary hydroperoxides have been found to be very effective for providing the free radicals required to maintain the chain reaction leading to the formation of cyclohexyl hydroperoxide. This peroxidation is referred to herein as "initiated" peroxidation since it is the addition of the tertiary hydroperoxide which "initiates" the reaction.

These tertiary hydroperoxides are normally obtained by the known process of oxidizing the corresponding isoalkanes.

This oxidation of isoalkanes is carried out according to well known procedures to produce the maximum practical amount of the tertiary hydroperoxide compared to the tertiary alcohol produced. This results in 60 to 70% hydroperoxide and 30 to 40% alcohol since a higher ratio of hydroperoxide is not practical.

As previously indicated, the main products of the catalytic oxidation of cyclohexane are cyclohexanol and cyclohexanone with only a small amount of cyclohexyl hydroperoxide, perhaps 5 to 10% of the cyclohexane reacted. The process of the present invention involving initiated peroxidation rather than catalytic oxidation results in the formation of 60 to 80% cyclohexyl hydroperoxide with small amounts of the alcohol and ketone. The specific reaction rate and product distribution can be influenced, to some extent, by the amount of the tertiary hydroperoxide that is used for initiating the reaction.

The tertiary hydroperoxide initiated oxidation of a secondary carbon atom in cyclohexane results in the formation of cyclohexyl hydroperoxide at a rate comparable to the rate of the catalytic process but with a greatly reduced rate of decomposition of the cyclohexyl hydroperoxide. This is indicated by the small percentage of cyclohexanol and cyclohexanone in the product. This also shows that the free radical oxidation of cyclohexane is based on the thermal decomposition of the tertiary hydroperoxide rather than on the catalytic decomposition of the cyclohexyl hydroperoxide to provide the free radicals.

The peroxidation of the present invention is carried out by air or enriched air (oxygen concentration between 20% and 70%) at 100° to 200° C. and preferably 130° to 160° C. A reactor pressure is used which allows the removal of reaction heat by evaporation of the unreacted excess cyclohexane. This is typically 700 to 1200 kPa. The oxygen concentration in the vent gases, after condensation of the vapors, should be maintained at a relatively low level, preferably 1% to 5%, for reasons of operational safety and optimum reaction performance. The reaction mixture should be substantially free of dissolved metal ions, particularly transition metals, which would catalyze the decomposition of the cyclohexyl hydroperoxide. The reaction rate can be increased either by increasing the reaction temperature or by increasing the concentration of the tertiary hydroperoxide initiator. When 1% to 2% of the tertiary hydroperoxide is used, about 25% of it decomposes to form free radicals. This results in a conversion of 6% to 8% in the peroxidation of the cyclohexane.

The initiated peroxidation is not limited to cyclohexane. The secondary carbon atoms in other cyclic and non-cyclic alkanes can also be oxidized to the corresponding hydroperoxide. For example, the direct oxidation of ethyl benzene is normally limited to 12% to 15% conversion. That is improved by using a tertiary hydroperoxide as an initiator to obtain a higher conversion and/or selectivity for ethyl-benzyl hydroperoxide.

The use of the tertiary hydroperoxide as initiator allows the non-catalytic peroxidation of cyclohexane to be carried out at lower temperatures and producing cyclohexyl hydroperoxide at high selectivity. Also, the achieved conversion of cyclohexane was higher than for the commercially used catalytic oxidations of cyclohexane.

The rate of oxidation is proportional to the reaction temperature and to the concentration of the initiator. To maintain the required reaction rate, these two independent variables have to be adjusted. The applicable temperature is limited by the desired selectivity of the secondary hydroperoxide while the cost of the initiator may limit its concentration in the reaction mixture.

Previous patents and literature in the 1960's, described a technique called co-oxidation, which can also be used to facilitate the oxidation of a slowly reacting hydrocarbon by the addition of a readily oxidizable compound. In the co-oxidation of isopentane and cyclohexane, both tertiary and secondary hydroperoxides are formed simultaneously which is not as effective as the proposed technique of initiated peroxidation of cyclohexane with tertiary amyl or butyl hydroperoxide.

The separate peroxidation of isobutane with the recovery of tertiary butyl hydroperoxide, followed by the initiated peroxidation of cyclohexane is more cost efficient than the co-oxidation process which has a slightly lower equipment cost. The co-oxidation is economically feasible only if a mixture of similar quantities of tertiary and secondary hydroperoxides is needed. In general, the products (alcohols/ketones) from the partial oxidation of the tertiary hydrocarbons are less valuable than the products from the secondary hydrocarbons. Therefore, economics would dictate the use of the minimum amount of initiator (tertiary hydroperoxide) required to achieve a commercially feasible production rate.

The process described thus far is the invention described and claimed in the previously mentioned U.S. Pat. No. 5,220,075. The present invention will now be described using the peroxidation of cyclohexane with a tertiary butyl hydroperoxide initiator formed from isobutane as the example. As shown in the drawing, liquid isobutane and gaseous oxygen, in the form of air or oxygen enriched air, are fed to the isobutane peroxidation reactor 12 where tertiary butyl hydroperoxide is formed together with some tertiary butyl alcohol. The effluent of this reactor goes to the isobutane distillation step 14, where the unreacted isobutane is separated and recycled back to the isobutane peroxidation step 12. Fresh make-up cyclohexane is added to the reboiler of the isobutane distillation 14 to dilute the tertiary butyl hydroperoxide which is withdrawn from the bottom of the distillation column 14. The bottoms of this column are fed to the cyclohexane peroxidation step 16. This cyclohexane peroxidation produces an effluent stream containing the cyclohexyl hydroperoxide product, unreacted cyclohexane, a small amount of cyclohexanol and cyclohexanone, the unreacted tertiary butyl hydroperoxide and the tertiary butyl alcohol that has formed from the initiator.

In the present invention, this effluent stream from the peroxidation step 16 is fed to the first azeotropic distillation step 18. The tertiary butyl alcohol and cyclohexane form a minimum boiling, binary azeotrope having a composition of about 35% alcohol and 65% cyclohexane with a boiling point of about 72° C. The first azeotrope is a relatively small stream which is removed overhead. This distillate may be processed in a variety of ways depending on whether the required by-product is tertiary butanol or isobutylene. The drawing shows a process scheme designed for the recovery of tertiary butanol.

According to the process scheme illustrated, the components of the first azeotrope are separated by an extractive distillation step 20 using a highly polar, high boiling solvent, for example a glycol. The overhead of the extractive distillation is cyclohexane which is recycled to the peroxidation reaction step 16. The bottoms of distillation step 20 are fed to a solvent stripping column 22 where the tertiary butanol is recovered as distillate and the high boiling solvent is removed as bottoms. The recovered solvent, bottoms of step 22, is recycled to the extractive distillation step 20. However, if the required by-product is isobutylene rather than tertiary butanol, then the first azeotrope, containing cyclohexane and tertiary butanol, would be fed to a catalytic dehydration reactor. In this reactor the tertiary butanol is converted to isobutylene and water which are easily separated from cyclohexane. The cyclohexane is recycled to the peroxidation step 16, while isobutylene may be sold as a monomer for poly-isobutene or converted to methyl-tertiary butyl ether (MTBE) used as a gasoline additive, octane improver.

The bottoms from the first azeotropic distillation step 18 are fed to the next azeotropic distillation step 24. The feed contains the cyclohexyl hydroperoxide, tertiary butyl hydroperoxide and the remaining cyclohexane. This stream is distilled to produce the minimum boiling azeotrope of about 95% cyclohexane and 5% tertiary butyl hydroperoxide as overhead with a boiling point of about 80° C. This overhead, which contains most of the unreacted cyclohexane, is then recycled back to the secondary peroxidation reaction step 16.

The bottoms from the second azeotropic distillation step 24 contain the product of cyclohexyl hydroperoxide (about 20%–30%) with small quantities of cyclohexanol, cyclohexanone and the by-products of acids, esters, etc. This concentrated stream of cyclohexyl hydroperoxide can be either catalytically decomposed to cyclohexanol/cyclohexanone or used for various syntheses, i.e. epoxidation. The most important commercial epoxidation involves the coproduction of cyclohexanol and cyclohexanone together with propylene oxide. Besides epoxidation, there are other syntheses for the utilization of hydroperoxides such as hydroxylation, ammoximation, etc. which can lead to the formation of valuable coproducts.

The peroxidation of the secondary hydrocarbon, cyclohexane, is carried out at relatively low conversion levels of less than 25% due to the instability of the by-products (alcohols and ketones) of the oxidation. Therefore, the availability of large amounts of the cyclohexane for recycle is inherent in the process. These large recycle streams are ideally suited for the separation of the tertiary hydroperoxide from the secondary hydroperoxide product. The maximum amount of unreacted tertiary butyl hydroperoxide which can be recovered for recycle is limited by the amount of unreacted cyclohexane in the effluent from the peroxidation reactor. The sum of the recoverable tertiary butyl hydroperoxide and of the amount consumed in the peroxidation is the economical amount that can be used as the initiator.

While the above description has been limited to the example of tertiary butyl hydroperoxide as the initiator, the principle of recovering tertiary hydroperoxides as a binary azeotrope with the hydrocarbon being used for the production of the secondary hydroperoxides is equally applicable for other tertiary hydroperoxides such as tertiary amyl hydroperoxide from isopentane and cumyl hydroperoxide from cumene. Also, although the example has specifically described the peroxidation of cyclohexane to cyclohexyl hydroperoxide, the invention is equally applicable to the peroxidation of other alkanes and cycloalkanes such as ethyl benzene to yield ethyl-benzyl hydroperoxide. However, one has to select the specific tertiary hydroperoxide which will form a binary azeotrope with the secondary hydrocarbon which is to be peroxidized.

The intentional recovery and recycle of the binary azeotrope allows the efficient use of the initiator at concentrations above what would otherwise be uneconomical. This process will minimize the consumption of the tertiary hydroperoxide and the formation of the low priced, alcohol by-product as well as the size and cost of the tertiary hydroperoxide plant. Therefore, the recycle of the initiator will lead to an improvement in the overall economics of secondary hydrocarbon peroxidation. Besides the economic incentive, the commercial application of tertiary hydroperoxide recycle requires the consideration of safety aspects. The safe handling of process streams containing tertiary hydroperoxides requires that the total concentration of hydroperoxides and diperoxides be kept below about 50% It so happens that the concentrations of the tertiary hydroperoxides in the binary azeotropes are well below their safety limit.

We claim:

1. A method for the peroxidation of secondary carbon in hydrocarbons selected from the group consisting of alkanes and cycloalkanes to produce secondary hydroperoxides comprising:
   a. peroxidizing said hydrocarbon with molecular oxygen at a temperature of from 100° to 200° C. in the presence of a tertiary hydroperoxide initiator containing no more than 50 mole percent tertiary alcohol and the amount of tertiary hydroperoxide is from 0.5 to 10 mole percent of said hydrocarbon to produce a mixture of said secondary hydroperoxide, an unreacted quantity of said hydrocarbon, as unreacted quantity of said tertiary hydroperoxide and said tertiary alcohol;
   b. subjecting said mixture to azeotropic distillation whereby first a minimum boiling binary azeotrope of said tertiary alcohol and a portion of said unreacted hydrocarbon is removed from said mixture as overhead leaving a bottoms containing said secondary hydroperoxide, remaining unreacted hydrocarbon and said unreacted quantity of tertiary hydroperoxide;
   c. subjecting said bottoms to a further azeotropic distillation whereby a second minimum boiling binary azeotrope of said tertiary hydroperoxide and at least a portion of said remaining unreacted hydrocarbon is removed from said bottoms as an overhead and recycling said second minimum boiling azeotrope to said peroxidizing step.

2. A method as claimed in claim 1 wherein said portion of unreacted hydrocarbon is separated from said first minimum boiling azeotrope and is recycled to said peroxidizing step.

3. A method as claimed in claim 2 wherein said separation comprises the step of extractive distillation.

4. A method as claimed in claim 2 wherein said separation comprises the step of dehydrating the tertiary alcohol to the corresponding olefin.

5. A method as recited in claim 1 wherein said hydrocarbon is selected from the group consisting of cyclohexane and ethyl benzene.

6. A method as claimed in claim 5 wherein said hydrocarbon is cyclohexane.

7. A method as claimed in claim 6 wherein said temperature is from 130° C. to 160° C.

8. A method as claimed in claim 7 wherein said peroxidation is at a pressure of 700 to 1200 kPa.

9. A method as recited in claim 1 wherein said tertiary hydroperoxide is selected from the group consisting of tertiary butyl hydroperoxide and tertiary amyl hydroperoxide.

10. A method for the peroxidation of cyclohexane to produce cyclohexyl hydroperoxide and to minimize the production of cyclohexanol and cyclohexanone comprising the steps of:
   a. oxidizing an isoalkane and producing a product containing a tertiary hydroperoxide and a tertiary alcohol wherein said tertiary hydroperoxide comprises at least 50 mole percent of said product,
   b. mixing said cyclohexane with said product to produce a mixture, said mixture containing from 1-5 mole percent of said tertiary hydroperoxide, and
   c. contacting said mixture with oxygen at a temperature of 100° to 200° C. to peroxidize said cyclohexane to form a second mixture containing cyclohexyl hydroperoxide, unreacted cyclohexane, unreacted tertiary hydroperoxide and tertiary alcohol;
   d. subjecting said second mixture to azeotropic distillation whereby a first minimum boiling point azeotrope of said tertiary alcohol and a portion of said unreacted hydrocarbon is removed as overhead leaving a first bottoms;
   e. subjecting said first bottoms to azeotropic distillation whereby a second minimum boiling azeotrope of said tertiary hydroperoxide and said unreacted hydrocarbon is removed as overhead and recycling said second minimum boiling azeotrope to said peroxidizing reaction step.

* * * * *